United States Patent [19]
Vromans et al.

[11] Patent Number: 6,054,145
[45] Date of Patent: Apr. 25, 2000

[54] MAKING DOSAGE UNITS USING LOW SHEAR GRANULATION

[75] Inventors: Herman Vromans; Hendrika Gerardina Maria Poels-Janssen, both of Oss, Netherlands

[73] Assignee: Akzo Nobel, N.V., Arnhem, Netherlands

[21] Appl. No.: 09/267,320

[22] Filed: Mar. 12, 1999

[30] Foreign Application Priority Data

Dec. 3, 1998 [EP] European Pat. Off. ............... 98200790

[51] Int. Cl.$^7$ ....................................... A61K 9/14
[52] U.S. Cl. .......................... 424/489; 424/470; 424/461; 424/469; 424/458
[58] Field of Search ............................. 514/170; 424/489, 424/471, 461, 473, 464

[56] References Cited

U.S. PATENT DOCUMENTS

| | | | |
|---|---|---|---|
| 4,914,089 | 4/1990 | Tax | 514/170 |
| 5,098,714 | 3/1992 | Wright et al. | 424/473 |
| 5,508,042 | 4/1996 | Oshlack et al. | |

FOREIGN PATENT DOCUMENTS

| | | |
|---|---|---|
| 0 707 848 A1 | 4/1996 | European Pat. Off. . |
| 0 722 730 | 7/1996 | European Pat. Off. . |
| WO96/09056 | 3/1996 | WIPO . |

*Primary Examiner*—Thurman K. Page
*Assistant Examiner*—William E. Benston, Jr.
*Attorney, Agent, or Firm*—Mary E. Gormley

[57] ABSTRACT

Disclosed is a process for the preparation of pharmaceutical dosage units containing as an active substance of from 0.005 to 1.0% by weight of micronised Org 30659, comprising (a) a mixing step comprising bringing into association the active substance and a suitable carrier to form a mixture, and (b) a granulating step in which the mixture is granulated to form agglomerates or granules by wetting the mixture with a binder liquid, the wetting being conducted under agitation, characterised in that the granulation step (b) is conducted so as to exert on the granules a shear force which does not exceed the tensile strength of the agglomerates or granules. The process leads to granules and tablets having an excellent content/uniformity.

7 Claims, 1 Drawing Sheet

6,054,145

MAKING DOSAGE UNITS USING LOW SHEAR GRANULATION

FIELD OF THE INVENTION

The invention is in the field of making pharmaceutical dosage units of micronised, low dose steroids. Particularly, the invention pertains to a process for the preparation of pharmaceutical dosage units containing as an active substance of from 0.005 to 1.0% by weight of micronised Org 30659 (11-methylene-17α-ethinyl-17β-hydroxy-oestra-4,15-diene-3-one), comprising (a) a mixing step comprising bringing into association the active substance and a suitable filler to form a mixture, and (b) a granulating step in which the mixture is granulated to form agglomerates or granules by wetting the mixture with a binder liquid, the wetting being conducted under agitation. Such wet granulation is distinguished from dry granulation in that water or organic solvents are applied in wet granulation to produce agglomerates or granules.

BACKGROUND OF THE INVENTION

A process as indicated above has been known from WO 96/09056, which teaches wet granulation as a method of making dosage units comprising low doses of desogestrel or Org 30659. This known process leads to an excellent product stability. However, in the case of Org 30659, it leaves room for improvement as regards content uniformity.

An insufficient content uniformity, i.e. the situation that not all of the dosage units have the same quantity of the active substance, is a problem frequently incurred when making dosage units of potent steroids, which are micronised and which require low doses only (Org 30659 being in the range of from 0.005 to 1.0 % by weight and preferably of from about 0.01 to 0.5 percent by weight of each pharmaceutical dosage unit). Such potent compounds do not always distribute entirely evenly throughout, e.g., a tableting mixture, which may result in some of the tablets having relatively high amounts of steroid (i.e. "superpotent tablets"), while others have very low amounts of steroid. The content uniformity required in order to make a product in compliance with the US Pharmacopoeia should be such that the relative standard deviation of the content of the active substance (RSD) is below 6%. This in order to produce discrete dosage units which are reliable as a vehicle to administer a minute quantity of the active substance with a high accuracy. In terms of validated evidence (i.e. the requirement in the pharmaceutical industry that by validation of processes and products it is warranted that each dosage unit contains an adequate amount of the active substance), it is desired in the industry to strive for a higher degree of homogeneity, and to maintain an even stricter limit, e.g. an RSD of below 3%. This is also desirable for the sake of the practical feasibility of manufacturing the dosage units at an industrial scale. For, it is important to strictly adhere to as low an RSD as possible and to have as few as possible occasional batches with an RSD above 6%. This to avoid having to reject batches containing expensive and medicinally active substances, as such a waste of material is undesirable for both economical and safety and health reasons.

Another important aspect related to content uniformity, is that of the Demixing Potential (DP) of the granulate. This parameter is determined by screening the granulate so as to obtain different granule size sieve fractions (for example nine fractions, ranging from <75μm to >800μm particle size), and determining the content of said sieve fractions as a percentage of the declared content of the granulate. The DP is 0 if all of the fractions are in compliance with the declared content, i.e., if they all have a content of 100% of the declared content. The concept and determination of DP is known in the art, see e.g. EP 503 521. The lower the DP value, the better, as a granulate with a low DP below 15% and preferably below 10%, clearly is not prone to exhibiting segregation and will hence yield dosage units having a good content uniformity.

When Org 30659 is processed into a granulate using the known process, employing conventional high shear granulation apparatus, the DP typically is of the order of 30–40%. According to the invention it has now been found that, surprisingly, this figure, as well as the content uniformity of the granulate and the resulting dosage units, can be substantially improved.

SUMMARY OF THE INVENTION

To this end, the invention provides a process of the aforementioned type, wherein the granulation step (b) is conducted so as to exert on the granules a shear force which does not exceed the tensile strength of the agglonerates or granules. Without detracting from the further description of the invention given below, this can be achieved, in a typical embodiment of the invention, by avoiding the regular high shear when conducting the granulation. This is a departure from what is generally done in the art, where advanced high shear mixers form a standard device to make granules that can be used for filling capsules or for being processed into tablets.

In the art of making pharmaceutical dosage units by (wet) granulation, high shear mixers have become a conventionally used apparatus in which mixing and granulating is conducted. This type of equipment has considerable advantages, notably as it leads to the optimal mixing of the constituents of a pharmaceutical formulation. Furthermore, the process is well-contained and the available modern equipment enables full in-process control. Surprisingly, in the case of micronised steroids such as Org 30659 present in a low amount, the granulation process leads to a better content uniformity if the actual granulation step, i.e. wetting with binder liquid, while applying agitation, is conducted with substantially lower shear than normally applied in the current high-shear mixers.

In accordance with the invention, it has been recognised that the initial granule strength is the critical parameter for obtaining good content uniformity. This is a surprising finding, as the person skilled in the art will normally apply as high agitation forces as possible, since this leads to a uniform mixture having a good particle size distribution, as the always occurring lumps of material are broken down. However, in the case of low dose Org 30659, it was found that when the process of WO 96/09056 is conducted in a high shear mixer in a normal fashion, the content uniformity cannot be steered to an RSD of below 3% and the DP typically is 30–40%. When following the process of the invention, an excellent DP of well below 10% and consequently favourable content uniformity is obtained.

Without wishing to be bound by theory, the applicant believes that from the results obtained with the present invention, the following mechanism for the demixing occurring under high shear can be deducted. After the addition of binder liquid to the mixture formed under (a), locally overwetted regions will exist. These regions of the mass will give rise to the majority of the largest granules. These initially formed lumps cannot withstand the forces exerted thereon by a high shear mixer. This leads to a constant destruction of agglomerates in which a constant rearrangement of primary particles will unavoidably take place. The state of densification and saturation in which agglomerates can survive, is reached at first for agglomerates containing small primary particles, and these are subsequently able to grow. As a result, the biggest granule particles consist of the smallest primary particles. When drug particles are relatively small as compared to the excipient particles, as is the case with micronised steroids, the coarse granules contain the highest concentrations of the active substance. In accordance with the invention, this destructive nucleation growth mechanism is circumvented, since by lowering the impact pressure of the impellor of a high shear mixer, the above demixing phenomena are avoided.

It is preferred according to the invention if the first step, i.e. mixing the ingredients, is conducted in a normal fashion, i.e. in a conventional high shear mixer applying the regular shear forces. Of course, the subsequent granulation step can be conducted in a different apparatus applying lower shear, it is preferred to use the same apparatus as with mixing, but to make it run at a lower speed and/or with different equipment, so as to have the required lower shear.

DETAILED DESCRIPTION OF THE INVENTION

Figure 1:
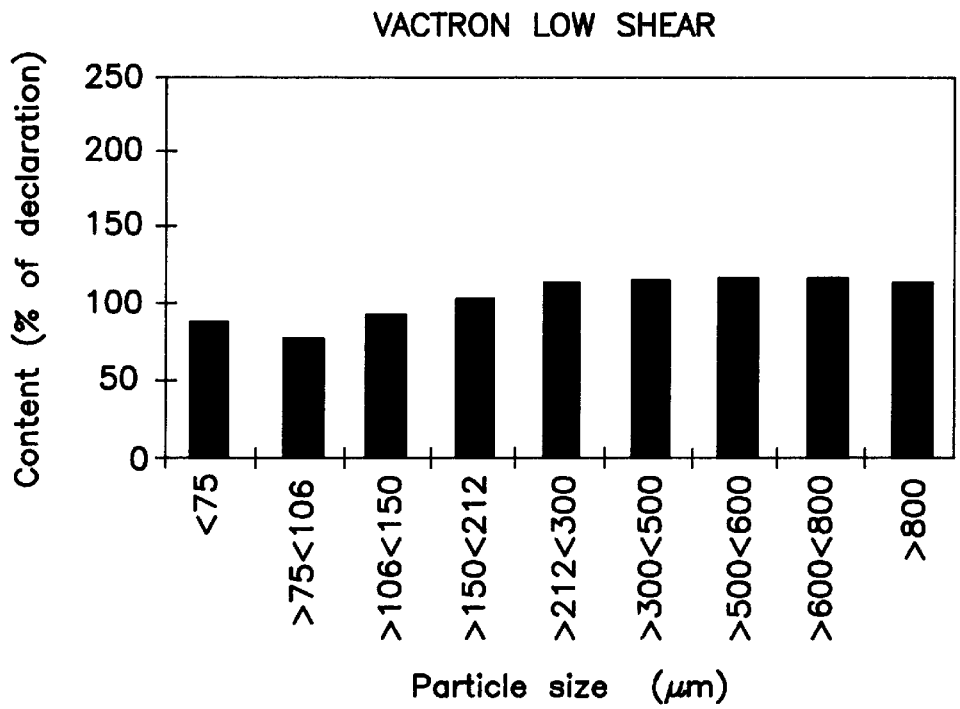

As indicated above, it is important for the applied shear forces not to exceed the initial granule strength. The (tear) strength of a granule is a concept well-known in the art, and the person of ordinary skill in the art knows how to determine it.

Depending on the amount of binding liquid (usually water) present in the mixed powder, several stages of granulation can be recognized, to which the following equations apply for the tensile strength $\tau$ of a granule (Rumpf Mechanische Verfahrenstechnik, Deutscher Verlag für Grundstoffindustrie, (1990) Leipzig)):

| Pendular state | $\tau_p = 9/4 \cdot (1 - \epsilon)/\epsilon \cdot \gamma/d \cdot \cos \alpha$ | (1) |
| Funicular state | $\tau_f = S \cdot 6 \cdot (1 - \epsilon)/\epsilon \cdot \gamma/d \cdot \cos \alpha$ | (2) |
| Capillary state | $\tau_c = 6 \cdot (1 - \epsilon)/\epsilon \cdot \gamma/d \cdot \cos \alpha$ | (3) | wherein $\epsilon$=porosity

S=level of void saturation $\gamma$=surface tension d=particle size cos $\alpha$=contact angle It should be noted that, in principle, it is possible for the applied shear forces to be increased during the process, as long as it is ensured that these forces do not exceed the granule strength at a given point in time. It is preferred, however, to determine the initial granule strength, i.e. the tensile strength of the associated material making up the mixture formed in the aforementioned mixing step (a), and to conduct the granulation by applying shear forces which are below the initial granule strength throughout the entire granulation step. It is then possible, and in fact preferred, to thereafter conduct a post-mixing step at high shear again (upon completion of the granulation the formed granules will have reached such a coherence and strength as to be capable of withstanding the normal shear forces of the high shear apparatus used).

In the regular apparatus, the applied shear forces are determined by the impact pressure $\sigma_i$ of the impellor tip of the high shear mixer, which can be estimated by:

$$\sigma_i = 0.5 \, \rho_s (\pi ND)^2 \quad (4)$$

wherein $\rho_s$=the density of solid (primary) particles

N=rotations per second

D=diameter of the impellor

The values for the initial granule porosity, the saturation, and the surface tension, can be determined by the person of ordinary skill in the art, upon which using the above equation (2) the initial tensile strength can be calculated. For a given apparatus, with a given mixing gear (such as an impeller, stirrer, or the like), the person skilled in the art can simply determine how to run the apparatus in order to have the required impact pressure using equation (4). This principally holds for any type apparatus and any mixing gear.

While the upper limit for the impact pressure is thus determined according to the present invention, the lower limit is not particularly critical. While 1000 N/m² can be given as a guideline for the lower limit, it is generally preferred that the impact pressure is as low as possible, as long as mixing can be suitably conducted. The latter is apparatus-dependent: it will be clear to the person skilled in the art, that a mixing gear having a shape that is optimised so as to lead to optimal mixing, can be made to work at a lower speed than a mixing gear that is less specialised. Hence, in the case, the impact pressure applied can generally be tuned to a minimum value, while in the second case a higher speed may be required, which usually will lead to a higher impact pressure. Similar considerations evidently hold for the degree of filling of the apparatus: the lower the degree of filling, the more relaxed the mixing requirements will be, hence the lower the resulting impact pressure. According to the invention it is preferred to apply an impact pressure not higher than 8000 N/m². In order to obtain optimal results in all circumstances, the impact pressure most preferably is chosen below 3000 N/m². The minimum value for the impact pressure, as a rule 1 N/m², is not particularly critical and will be determined mainly by the type of apparatus, i.e. as indicated above, the better the mixing function of the apparatus, the lower the speed one can apply, hence the lower the shear force exerted on the granules.

After the granulation process according to the invention, the resulting granules can be used for filling capsules, or for being processed into tablets or other types of solid dosage units. Methods for making tablets and other solid or dry pharmaceutical preparations are well-known. For example in the standard English language text Gennaro et al., Remington's Pharmaceutical Sciences, (18th ed., Mack Publishing Company, 1990, see especially Part 8: Pharmaceutical Preparations and Their Manufacture), methods of making tablets, capsules and pills and their respective components are described.

Depending on the specific utility, the progestogen Org 30659 can be admixed with other active substances, notably estrogens, which are preferably selected from ethinyl estradiol (EE), estradiol, and mestranol. Most preferred are tablets comprising Org 30659 and ethinyl estradiol.

Apart from satisfying the above indicated "low-shear" requirement, the process of the invention can be conducted as a regular wet-massing method in which a liquid is added to a powder or granulate in a vessel equipped with any type of agitation that will provide granules or agglomerates. Various operations can be recognised in the wet (massing) granulation, including milling of drugs and excipients, mixing of milled powders, preparation of binder solution, mixing the binder solution with the powder mixture to form the wet mass, coarse screening of wet mass, drying moist granules, screening dry granules, mixing the screened granules with lubricant and disintegrant, and finally filling the granulate into capsules or compressing the granulate to tablets. It is obvious that, depending on the selected excipients and the size of the batch and the selected equipment, some of the operations can be combined or are not required or particular operations can be included. General methods of preparing granules are for instance described in Pharmaceutical Dosage Forms: Tablets (Volume I). Ed. H. A. Lieberman, L. Lachman, J. B. Schwartz (1989), Marcel Dekker Inc. New York and Basel pp. 131–190.

Advantages of wet granulation, which are retained with the process of the invention, include improvement of the cohesiveness and compressibility of powders, a good distribution and uniform content of micronised or finely milled low-dosage drugs, reduction of a great deal of dust and airborne contamination, prevention of segregation of components.

Small-scale production can be achieved by mixing and wetting the mass in mortars or stainless steel bowls, whereas for larger quantities twin-shell blenders, double-cone blenders, planetary mixers, rotary granulators and high shear mixers can be applied. General mixing methods are disclosed in Pharmaceutical Dosage Forms (Volume 2). Ed. H. A. Lieberman, L. Lachman, J. B. Schwartz (1990), Marcel Dekker Inc. New York and Basel pp. 1–71. The dry excipients and the micronised or finely milled active ingredients are mixed in a suitable mixer, preferably a mixer in which both mixing and granulating can be performed, for instance a Gral high shear mixer, after which an aqueous binder solution is added. Another preferred method is suspending the active ingredients into the aqueous binder solution, which suspension is added to the dry mixture of excipients and granulated.

Granulates and tablets prepared by wet-granulation consist of several inert materials that can be found in conventional solid oral dosage forms in general. The ingredients can be classified in excipients which help to impart satisfactory processing and compression characteristics to the formulation like diluents, binders, glidants and lubricants and in excipients to give the desirable physical characteristics to the finished tablet like disintegrants and colors. If required the tablets can be provided with a film coat, for instance as disclosed in Pharmaceutical Dosage Forms (Volume 3). Ed. H. A. Lieberman, L. Lachman, J. B. Schwartz (1990), Marcel Dekker Inc. New York and Basel pp. 93–125.

Fillers (sometimes referred to as carriers, diluents, or bulking agents) usually make up the major portion of the tablet. The group of most commonly used fillers include the water insoluble calcium phosphates (di- and tribasic), calcium sulfate dihydrate, calcium carbonate, starch, modified starches and microcrystalline cellulose and the water soluble lactose, sucrose, dextrose, mannitol and sorbitol.

The substances that bind powders together and provide cohesiveness to the tablet formulation are binding agents or adhesives. Binders can be added dry and blended with the diluents and the drug. In this case binders are activated by addition of water or other solvents. In other manufacturing procedures, the adhesives are dissolved or slurried in a liquid and, in this form, added to the mixed powders. Conventional binders include gelatin, water soluble modified starch, and sugars as sucrose, glucose, dextrose, molasses and lactose. Natural and synthetic gums which have been used include tragacanth, magnesium aluminium silicate, acacia, ammonium calcium alginate, sodium alginate, carboxymethylcellulose, hydroxypropylcellulose, methylcellulose, hydroxypropylmethylcellulose, polyvinylpyrrolidone, polyethylene glycol and clays like Veegum.

Depending on, for example, the solubility of the binders in the various liquids, the binder can be added to the powder mix as a solution in water, a water-solvent mixture and in a organic solvent.

Materials to improve the flow characteristics are referred to as glidants. As an example, silicon dioxide, magnesium lauryl sulfate, magnesium aluminium silicate, magnesium oxide, talc or clays can be incorporated into the formulation to reduce inter-particulate friction and to eliminate the problems associated with the flow of materials from larger to smaller apertures in the tablet presses.

Before filling capsules or sachets, or compressing tablets, lubricants are mostly added to prevent friction and wear during processing. Some of the lubricants also demonstrate anti-adherent properties that can be relevant in case of sticking of tablet granulations to the faces of the punches and the die walls. Examples of the group of lubricants are the metallic stearates (magnesium stearate), talcum, stearic acid, sodium stearyl fumarate, hydrogenated vegetable oil, and high melting point waxes.

A component incorporated into the tablets to help the tablet to break up and dissolve to release the active component is the disintegrant. The total amount of disintegrant can be added to the granulation just prior to compression, can be added to the total mass of powdered materials before the wet granulation process takes place or can be simply divided into one portion added before wet granulation and one portion added dry to the granulates. Examples of the group of disintegrants that can be applied are starch, alginic acid, sodium starch glycolate, guar gum, croscarmellose sodium, crosslinked polyvinylpyrrolidone and ion exchange resins.

The dosage units, preferably tablets, obtained by the process of this invention are free from organic solvents, and comprise Org 30659, present in an amount of about 0.005 to 1.0 percent by weight of each pharmaceutical dosage unit, a small amount being less than 20% (e.g. 0.5–20%), and preferably less than 10% by weight of water, and optionally an estrogen. Preferably the estrogen is ethinyl estradiol or estradiol. The amount of water can vary and depends from the drying conditions and the composition of the dosage form applied. The tablets, however, always possess trace amounts of water, usually less than 10% by weight, and preferably about 0.5 to 8% by weight.

In view of the difficulty in processing the present compound Org 30659 into a granulate having a DP of below 15% and into dosage units having a content uniformity of below 3%, these results have not been achieved before in the art. Hence, the invention also pertains to the resulting novel products. Accordingly, one such novel product is a granulate comprising Org 30659 associated with a suitable carrier, which is characterized by having a DP of below 15%, and in a preferred embodiment of below 10%. This granulate is excellently suitable for filling capsules, and for further processing into tablets having a good content-uniformity. The other novel product according to the invention is a package comprising a plurality of n tablets, n being an integer of at least 10, having a uniform content of Org 30659 in that the RSD is below 3%.

The invention is further explained hereinafter with reference to the following examples and Figures.

EXAMPLE 1

Low shear granulation of a tabletting composition containing Org 30659 and EE.

| Composition core: | Org 30659 (micronised) | 0.180 mg |
|---|---|---|
| | EE (micronised) | 0.015 mg |
| | HPC | 1.950 mg |
| | Corn starch | 9.750 mg |
| | Lactose 200M | 52.780 mg |
| | Mg stearate | 0.325 mg |
| | Mass tablet core | 65.00 mg |
| Composition coat: | HPMC E15 | 0.75 mg |
| | PEG 400 | 0.15 mg |
| | Talcum | 0.19 mg |
| | Titanium dioxide | 0.11 mg |
| | Total tablet mass | 66.2 mg |

Pre-mix

Transfer in a 2 l glass container lactose 200M (125 g), Org 30659 (70.356 g) and EE (5.810 g) mix for 30 minutes in Turbula T2C(container mixer) at 22 rpm. Add to this mixture lactose 200M (125 g) and mix again for 30 minutes in Turbula T2C (container mixer) at 22 rpm.

Finally add lactose 200M (500 g) and mix for 30 minutes in Turbula T2C(container mixer) at 22 rpm.

Pass this mixture over a 106 μm screen using a Retsch VE 1000 sieve apparatus.

Vactron Granulation Process

Transfer the remainder part of lactose 200M (19799 g) and corn starch (3750 g) to the Vactron and mix for 3 minutes at an impeller speed of 150 rpm and a breaker speed of 1500 rpm.

Add the pre-mix with Org 30659 and EE to the lactose 200M, corn starch mixture and mix for 3 minutes with an impeller speed of 150 rpm. The breaker is not used.

Prepare the granulation liquid by dissolving/suspending HPC (750 g) in water (4375 ml) while stirring.

Transfer the HPC mucilage to the powder mass and mix meanwhile with an impeller speed of 75 rpm and a breaker speed of 300 rpm. The impact pressure thus caused by the impeller is 2600 N/m$^2$. Granulate for 30 minutes.

Continue the granulation process for 1 minute with an impeller speed of 150 rpm and a breaker speed of 1500 rpm to reduce the agglomerates in the granulate.

Vactron Drying Procedure

The product is dried at elevated temperature under a pressure of 50 mbar. To reduce agglomerates stop the dry procedure after 10 minutes and mix the granulate for 1 minute at an impeller speed of 150 rpm and a breaker speed of 1500 rpm. Continue the dry procedure until the product has reached a temperature of 40° C.

Sieving of the Dried Mass

Classify the granulate using a Comil sieving apparatus provided with a 050G screen and 1601 impeller.

Homogenise the sieved granulate in a 10 l vessel on Rhönrad tumble mixer for 10 minutes.

Admixing of the Granulate with Magnesium Stearate

Admix the sieved and homogenised granulate with magnesium stearate (0.5%m/m, particles <710 μm) in a suitable vessel on a Rhönrad tumble mixer for 10 minutes.

Tabletting Procedure

Compress the granulate on a Korsch PH106 rotary tabletting machine to tablets with a mass of 65 mg a diameter of 5 mm and a radius of convexity 1.1 and 9.5 mm and a crushing strength of 35 to 45 N.

Coating Procedure

Tablet cores are provided in the Glatt labcoater with an Opa-dry (OY-S-28833) aqueous film-coat consisting of HPMC E-15, PEG 400, talcum and titanium dioxide.

| | | Results | |
|---|---|---|---|
| particles (μm) | fraction (%) | content Org 30659 (%) | content EE (%) |
| d < 75 | 32 | 83 | 76 |
| 75 < d < 106 | 17 | 104 | 90 |
| 106 < d < 150 | 14 | 113 | 99 |
| 150 < d < 212 | 9 | 112 | 99 |
| 212 < d < 300 | 6 | 112 | 99 |
| 300 < d < 500 | 9 | 110 | 98 |
| 500 < d < 600 | 4 | 108 | 96 |
| 600 < d < 800 | 6 | 106 | 95 |
| d > 800 | 3 | 104 | 92 |
| demixing potential | | 12 | 11 |

| | | Content Org 30659/EE | | | | |
|---|---|---|---|---|---|---|
| Sample | | Org 30659 (μg) | rsd (%) | % of decl. | EE (μg) | rsd (%) | % of decl. |
| granulate after Comil | (n = 10, 200 mg) | 177.1 | 0.5 | 98 | 13.3 | 0.7 | 88 |
| coated tablets | mean cont. (3 × 10) | 178.9 | 0.5 | 99 | 13.5 | 0.5 | 90 |
| coated tablets | content uniformity (10 × 1) | 172.1 | 2.7 | 96 | 13.7 | 2.9 | 91 |

EXAMPLE 2

Low shear granulation of a tabletting composition containing Org 30659 and E2.

| Composition core: | Org 30659 (micro) | 0.0075 mg |
|---|---|---|
| | E2 (micro) | 1.000 mg |
| | HPC | 1.950 mg |
| | Corn starch | 9.750 mg |
| | Lactose 200M | 51.9675 mg |
| | Mg stearate | 0.325 mg |
| | Mass tablet core | 65.00 mg |
| Composition coat: | HPMC E15 | 0.75 mg |
| | PEG400 | 0.15 mg |
| | Talcum | 0.19 mg |
| | Titanium dioxide | 0.11 mg |
| | Total tablet mass | 66.2 mg |

Pre-mix

Transfer in a 1 l glass container lactose 200M (125 g) and Org 30659 (2.93 g) mix for 30 minutes in a Turbula T2C(container mixer) at 22 rpm. Add to this mixture lactose 200M (125 g) and mix again for 30 minutes in a Turbula T2C(container mixer) at 22 rpm.

Transfer this mixture in a 2 l glass container add lactose 200M (250 g) and mix for another 30 minutes in the Turbula T2C(container mixer) at 22 rpm. Pass this mixture over a 106 μm screen using a Retsch VE 1000 sieve apparatus. Transfer in a Muller vessel (10 l) lactose 200M (5000 g), Estradiol (400.64 g) and the pre-mix of Org 30659.

Mix the Muller vessel and content for 60 minutes on a Rhönrad tumble mixer.

Vactron Granulation Process

Transfer the remainder part of lactose 200M (14471 g) and corn starch (3750 g) to the Vactron and mix for 5 minutes at an impeller speed of 150 rpm and a breaker speed of 1500 rpm.

Add the mixture of Org 30659, E2 and lactose 200M to the mixture of lactose 200M and corn starch and mix for 10 minutes with an impeller speed of 150 rpm and a breaker speed of 1500 rpm.

Prepare the granulation liquid by dissolving/suspending HPC (750 g) in water (4300 ml) while stirring.

Transfer the HPC mucilage to the powder mixture and mix meanwhile with an impeller speed of 75 rpm and a breaker speed of 300 rpm. The impact pressure thus caused by the impeller is 2600 N/m$^2$. Granulate for 30 minutes.

Vactron Drying Procedure

The product is dried at elevated temperature under a pressure of 50 mbar. To reduce agglomerates stop the dry procedure after 10 minutes and mix the granulate for 1 minute at an impeller speed of 150 rpm and a breaker speed of 1500 rpm. Continue the dry procedure until the product has reached a temperature of 40° C.

The remainder of the procedure (sieving, admixing with magnesium stearate, tabletting, and coating: as in Example 1.

Results

| particle size (μm) | fraction (%) | content Org 30659 (%) | content E2 (%) |
|---|---|---|---|
| d < 75 | 25 | 83 | 77 |
| 75 < d < 106 | 15 | 96 | 85 |
| 106 < d < 150 | 16 | 111 | 98 |
| 150 < d < 212 | 13 | 117 | 102 |
| 212 < d < 300 | 7 | 109 | 104 |
| 300 < d < 500 | 10 | 117 | 104 |
| 500 < d < 600 | 5 | 117 | 104 |
| 600 < d < 800 | 7 | 114 | 102 |
| d > 800 | 4 | 112 | 102 |
| demixing potential (%) | | 13 | 12 |

Content Org 30659/E2

| Sample | | Org 30659 (μg) | rsd (%) | % of decl. | E2 (μg) | rsd (%) | % of decl. |
|---|---|---|---|---|---|---|---|
| granulate after Comil | (n = 10, 200 mg) | 7.28 | 3.3 | 97 | 973 | 5.3 | 97 |
| coated tablets | mean cont. (3 × 10) | 7.28 | 0.9 | 97 | 997 | 0.4 | 100 |
| coated tablets | content uniformity (20 × 1) | 7.23 | 2.6 | 96 | 1003 | 2.6 | 100 |

EXAMPLE 3

Low shear granulation of a tabletting composition containing Org 30659.

| Composition: | Org 30659 (micro) | 0.0075 mg |
|---|---|---|
| | HPC | 1.950 mg |
| | Corn starch | 9.750 mg |
| | Lactose 200M | 52.9675 mg |
| | Mg stearate | 0.325 mg |
| | Mass tablet core | 65.00 mg |

Pre-mix

Transfer in a container (75×130 mm) lactose 200M (125 g) and Org 30659 (2.347 g) and mix for 30 minutes in Turbula T2C(container mixer) at 22 rpm. Transfer this mixture in a glass container (1 l) and lactose 200M (125 g) mix for 30 minutes in Turbula T2C(container mixer) at 22 rpm.

Transfer the above mentioned mixture in a glass (2 l) container add lactose 200M (250 g) and finally mix for 30 minutes in Turbula T2C(container mixer) at 22 rpm.

Pass this mixture over a 106 μm screen using a Retsch VE 1000 sieve apparatus.

Vactron Granulation Process

Transfer the remainder part of lactose 200M (15798 g) and corn starch (3000 g) to the Vactron and mix for 5 minutes at an impeller speed of 150 rpm and a breaker speed of 1500 rpm.

Add the pre mix with Org 30659 to the lactose 200M, corn starch mixture and mix for 3 minutes with an impeller speed of 150 rpm. The breaker is not used. Prepare the granulation liquid by dissolving/suspending HPC (600 g) in water (3500 ml) while stirring.

Transfer the HPC mucilage to the powder mass and mix meanwhile with an impeller speed of 75 rpm and a breaker speed of 300 rpm. Granulate for 30 minutes. Continue the granulation process for 1 minute with an impeller speed of 150 rpm and a breaker speed of 1500 rpm to reduce the agglomerates in the granulate.

The remainder of the procedure (drying, sieving, admixing with magnesium stearate, tabletting, and coating): as in Example 1.

Results

See FIG. 1, depicting the content of Org 30659 as a function of the granule size fraction for a batch processed in the Vactron at 75 rpm. The content is 7.5 μg per 65 mg. Demixing potential =15%, tablet content uniformity RSD= 2.8%

Comparative Example A

Conventional granulation of a tabletting composition containing Org 30659 and E2.

| Composition granulate: | Org 30659 (micro) | 0.0225 mg |
|---|---|---|
| | Estradiol (micro) | 3.000 mg |
| | HPC | 1.950 mg |
| | Lactose 200M | 60.0275 mg |
| | Total mass | 65.00 mg |

Pre-mix

Transfer in a Muller vessel (10 l) lactose 200M (5000 g), Org 30659 (8.65 g) and Estradiol (1195.7 g)

Mix the Muller vessel with content for 60 minutes on a Rhönrad tumble mixer.

Vactron Granulation Process

Transfer HPC (750 g) and the remainder part of lactose 200M (18046 g) to the Vactron and mix for 10 minutes at an impeller speed of 150 rpm and a breaker speed of 1500 rpm.

Add the pre mix with lactose 200M, Org 30659 and E2 to the lactose 200M, HPC mixture and mix for 10 minutes with an impeller speed of 150 rpm and a breaker speed of 1500 rpm.

Transfer the granulation liquid water (2500 ml) in about 7 minutes to the powder mass and mix meanwhile with an impeller speed of 150 rpm and a breaker speed of 1500 rpm. Granulate for an additional 10 minutes with an impeller speed of 250 rpm and a breaker speed of 1500 rpm.

Vactron Drying Procedure

Before starting the drying procedure homogenise the granulate for 2 minutes with an impeller speed of 50 rpm and a breaker speed of 1500 rpm. Drying as above.

Sieving of the Dried Mass

As in Example 1.

| Results | | | |
|---|---|---|---|
| particles (μm) | fraction (%) | Cont. Org 30659 (%) | Cont. E2 (%) |
| d < 75 | 9.2 | 28.7 | 25.5 |
| 75 < d < 106 | 12.6 | 26.4 | 22.8 |
| 106 < d < 150 | 10.6 | 28.7 | 24.5 |
| 150 < d < 212 | 8.4 | 34.9 | 31.3 |
| 212 < d < 300 | 1.1 | 74.1 | 71.9 |
| 300 < d < 500 | 6.8 | 140.9 | 139.3 |
| 500 < d < 800 | 36.4 | 145.5 | 143.3 |
| 800 < d < 1000 | 10.6 | 144.0 | 142.0 |
| d > 1000 | 4.4 | 136.7 | 136.0 |
| demixing potential | | 58.3 | 60.9 |

In view of the high demixing potential, further tabletting was refrained from.

Comparative Example B

Conventional granulation of a tabletting composition containing Org 30659 and E2.

| Composition: | Org 30659 (micro) | 0.0075 mg |
|---|---|---|
| | Estradiol (micro) | 2.000 mg |
| | HPC | 1.950 mg |
| | Corn starch | 9.750 mg |
| | Lactose 100M | 50.9675 mg |
| | Mg stearate | 0.325 mg |
| | Mass tablet core | 65.00 mg |

Pre-mix

Transfer in a Muller vessel (20 l) lactose 100M (5000 g), Org 30659 (2.93 g) and Estradiol (797.1 g) Mix the Muller vessel with content for 60 minutes on a Rhönrad tumble mixer.

Vactron Granulation Process

Transfer the remainder part of lactose 200M (14570 g), HPC (250 g) and corn starch (3750 g) to the Vactron and mix for 10 minutes at an impeller speed of 150 rpm and a breaker speed of 1500 rpm.

Add the pre-mix with Org 30659 and Estradiol to the lactose 100M, corn starch mixture and mix for 10 minutes with an impeller speed of 150 rpm and a breaker speed of 1500 rpm.

Prepare the granulation liquid by dissolving/suspending HPC (500 g) in water (2000 ml) while stirring.

Transfer the HPC mucilage to the powder mass and mix meanwhile with an impeller speed of 150 rpm and a breaker speed of 1500 rpm . Granulate for 7.5 minutes with an impeller of 250 rpm and a breaker speed of 1500 rpm for 7.5 minutes.

Vactron Drying Procedure

Before starting the drying procedure homogenise the granulate for 2 minutes with an impeller speed of 50 rpm and a breaker speed of 1500 rpm. Drying as above.

Sieving of the Dried Mass

As in Example 1.

Admixing of the Granulate with Magnesium Stearate

Admix the sieved and homogenised granulate with magnesium stearate (0.5%m/m, particles <710 μm) in a suitable vessel on a Rhönrad tumble mixer for 5 minutes.

Tabletting Procedure

As in Example 1.

Results

Figure 2:
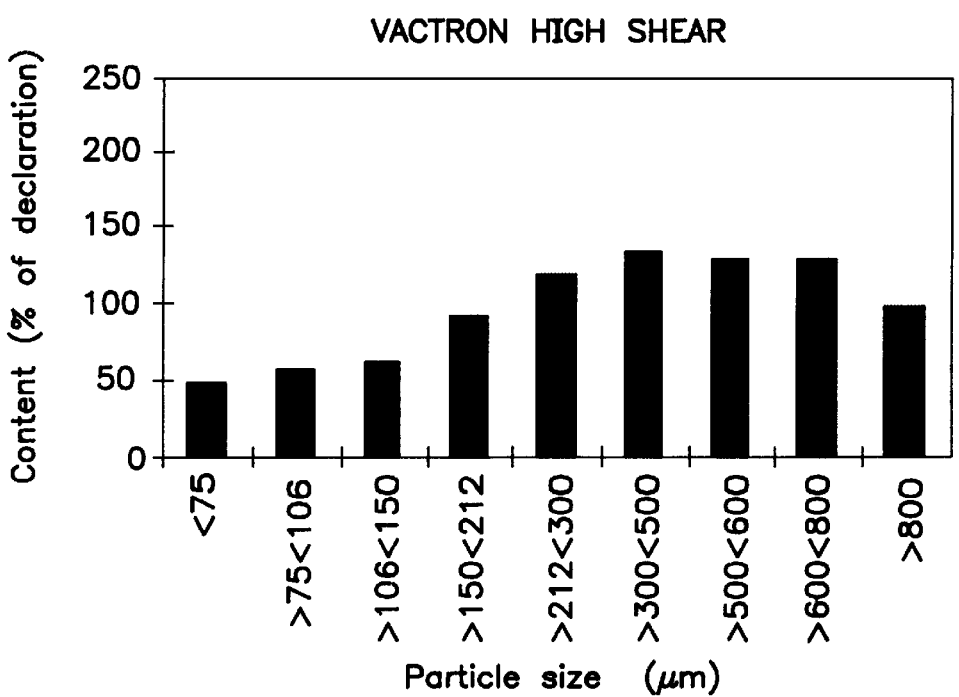

See FIG. 2, depicting the content of Org 30659 as a function of the granule size fraction of a granulate processed in the Vactron high shear mixer. Demixing potential 38% Granulate content uniformity RSD=3.9%, tablet content uniformity RSD=3.6%.

Comparative Example C

Conventional granulation of a tabletting composition containing Org 30659 and EE.

| Composition: | Org 30659 (micronised) | 0.0075 mg |
|---|---|---|
| | Ethinyl estradiol (micronised) | 2.000 mg |
| | HPC | 1.950 mg |
| | Corn starch | 13.0 mg |
| | Lactose 200M | 49.695 mg |
| | Mg stearate | 0.325 mg |
| | Mass tablet core | 65.00 mg |
| Composition coat: | HPMC E15 | 0.75 mg |
| | PEG400 | 0.15 mg |
| | Talcum | 0.19 mg |
| | Titanium dioxide | 0.11 mg |
| | Demineralised water | to 15 μl |
| | Total tablet mass | 66.2 mg |

Manufacturing Procedure

Prepare the batch in a Gral 25 high speed granulator.

A. Fill the granulator with lactose 200 M (2476.5 g) and corn starch (650.0) and mix for 1 minute at 460 rpm.

B. Dissolve in a beaker HPC (97.5 g) in 325 g of water and store it at 4° C. until it is free of air bubbles.

C. Transfer in a beaker part of the mucilage (9.75 g), add water (115 ml) and mix for 1 minute at 10,000 rpm.

D. Allow the arisen foam to disappear and add carefully Org 30659 micronised (9.0 g) and EE micronised (0.75 g) to this mucilage. To rinse the used containers transfer the remainder part of water herein and shake vigorously. Transfer this suspension/solution also in the beaker.

E. Suspend Org 30659 and EE in the aqueous mucilage by using a turrax with stirrer for 5 minutes by increasing the stirring speed gradually till a rotation speed of 10,000 rpm is reached.

F. Allow the arisen foam to disappear and transfer this suspension in a glass beaker with the remainder part of HPC mucilage. Rinse stirrer and beaker with water and transfer this suspension/solution in the beaker with Org 30659/EE suspension and HPC mucilage.

G. Stir this mucilage for 60 minutes at 2000 rpm using a stirrer equipped with the horizontal blade blender.

H. Add the Org 30659/EE suspension quantitatively to the mass (A) and granulate for 2 minutes at 460 rpm. Continue granulation for an additional 6 minutes at 460 rpm.

I. Dry the mass (H) in a vacuum cabinet for 4 hours under diminished pressure at 40° C.

J. Pass the dried mass (I) through a 710 μm sieve using an oscillating sieve.

K. Transfer the weighed granulate (J) in a 2 liter glass container and mix for 5 minutes with 0.5% magnesium stearate (passed through a 710 μm sieve) at 32 rpm using the Turbula T2C mixer.

L. Tabletting and coating as above.

Results:

Content uniformity of the tablets (n=20)

| Org 30659: | 99.1% | RSD = 7.3 |
| EE: | 97.3% | RSD = 7.0 |

We claim:

1. A process for the preparation of pharmaceutical dosage units containing as an active substance of from 0.005 to 1.0% by weight of micronised Org 30659, comprising (a) a mixing step comprising bringing into association the active substance and a suitable filler to form a mixture, and (b) a granulating step in which the mixture is granulated to form agglomerates or granules by wetting the mixture with a binder liquid, the wetting being conducted under agitation, wherein the granulation step (b) is conducted so as to exert on the granules a shear force which does not exceed the tensile strength of the aggolomerates or granules.

2. A process according to claim 1, wherein the force applied during step (b) does not exceed the tensile strength of the associated material making up the mixture formed in step (a).

3. A process according to claim 2, wherein the granulating step (b) is followed by a post-mixing step (c).

4. A process according to any one of claims 1–3, wherein all of the steps are conducted in a high-shear mixer, suitably operated at different speeds.

5. A process according to 4, wherein impact pressure of the impellor tip of the high-shear mixer is lower than 8000 $N/m^2$.

6. A granulate comprising 0.005 to 1.0% by weight of micronised Org 30659 associated with a suitable filler, and which has a DP (Demixing Potential) of below 15%.

7. A package comprising a plurality of n tablets, n being an interger of at least 10, the tablets comprising 0.005 to 1.0% by weight of micronised Org 30659, wherein the tablets in the package have a uniform content of Org 30659 such that the RSD (relative standard deviation) is below 3%.

* * * * *